United States Patent [19]

Kim

[11] Patent Number: 5,569,216
[45] Date of Patent: Oct. 29, 1996

[54] MULTIPURPOSE COLOSTOMY DEVICE HAVING BALLOONS ON AN END THEREOF

[76] Inventor: Jae H. Kim, Bosung Hwangsil Town 109-701, Namsan-Dong, Joong-Ku, Taegu, Rep. of Korea

[21] Appl. No.: 352,071

[22] Filed: Nov. 30, 1994

[30] Foreign Application Priority Data

Dec. 2, 1993 [KR] Rep. of Korea ............... UM93-26400
Aug. 18, 1994 [KR] Rep. of Korea ............... UM94-21031

[51] Int. Cl.$^6$ ............................ A61M 31/00; A61F 5/44; A61F 2/00
[52] U.S. Cl. ............................ 604/277; 604/334; 600/29
[58] Field of Search ................................ 600/28, 29, 30, 600/31; 604/277, 334, 95–102, 332

[56] References Cited

U.S. PATENT DOCUMENTS

| | | | |
|---|---|---|---|
| 1,965,653 | 7/1934 | Kennedy | 600/29 |
| 2,457,244 | 12/1948 | Lamson | 600/29 |
| 3,543,744 | 11/1968 | LePar | 604/277 |
| 4,460,363 | 7/1984 | Steer et al. | 604/336 |
| 4,721,508 | 1/1988 | Burton | 604/277 |
| 5,306,226 | 4/1994 | Salama | 600/29 |

FOREIGN PATENT DOCUMENTS 1212904 11/1970 United Kingdom.

*Primary Examiner*—David H. Willse
*Assistant Examiner*—David J. Cho
*Attorney, Agent, or Firm*—Birch, Stewart, Kolasch & Birch, LLP

[57] ABSTRACT

A multipurpose colostomy device for fixing in the stoma or rectum of a human body, includes an internal balloon, a ring configured external balloon surrounding the internal balloon, a connecting tube disposed under the both internal and external balloons, a joint tube operatively connected to a drainage hose and disposed under connecting tube, a supporting plate disposed between the connecting and joint tubes for fixing the colostomy to the abdominal wall, and an L-shaped supply tube containing a pair of air passages, a washing fluid passage and an enema fluid passage.

12 Claims, 4 Drawing Sheets

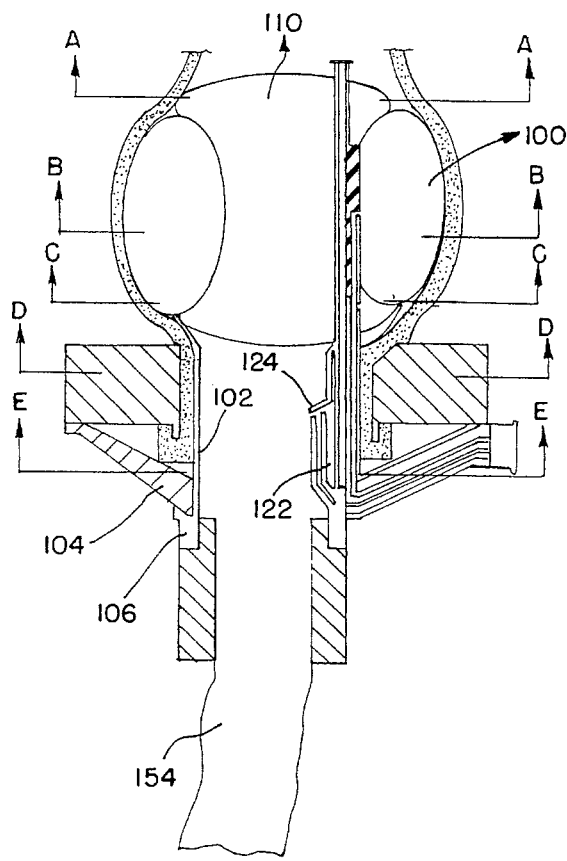
FIG. 5
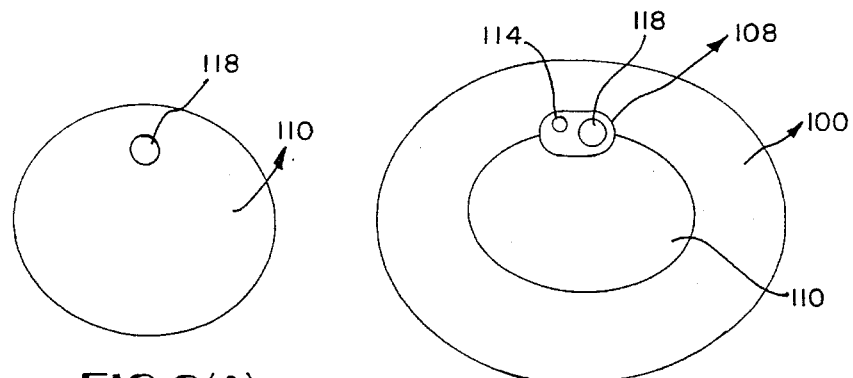
FIG. 6(A)  FIG. 6(B)
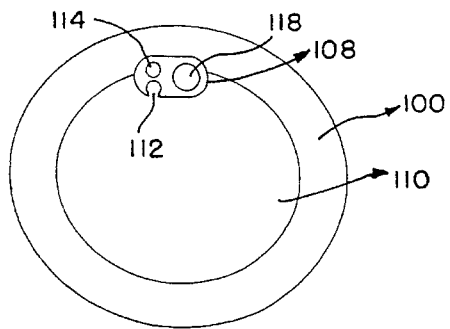 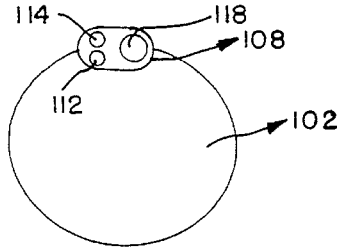
FIG. 6(C)  FIG. 6(D)

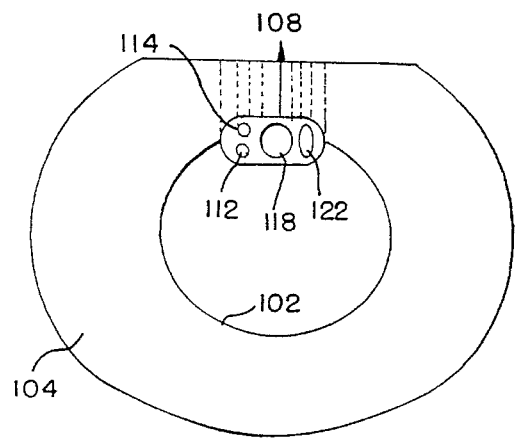
FIG.6(E)
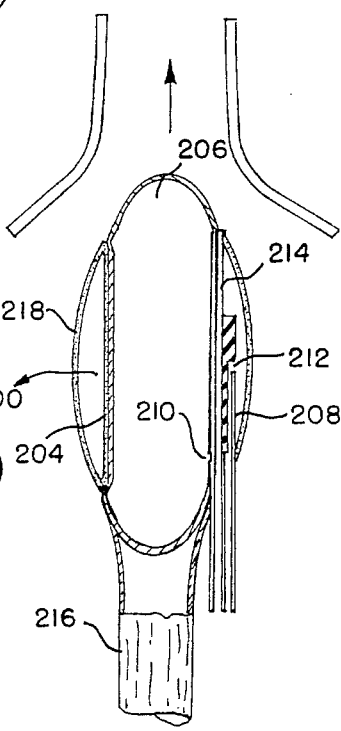
FIG.7(A)
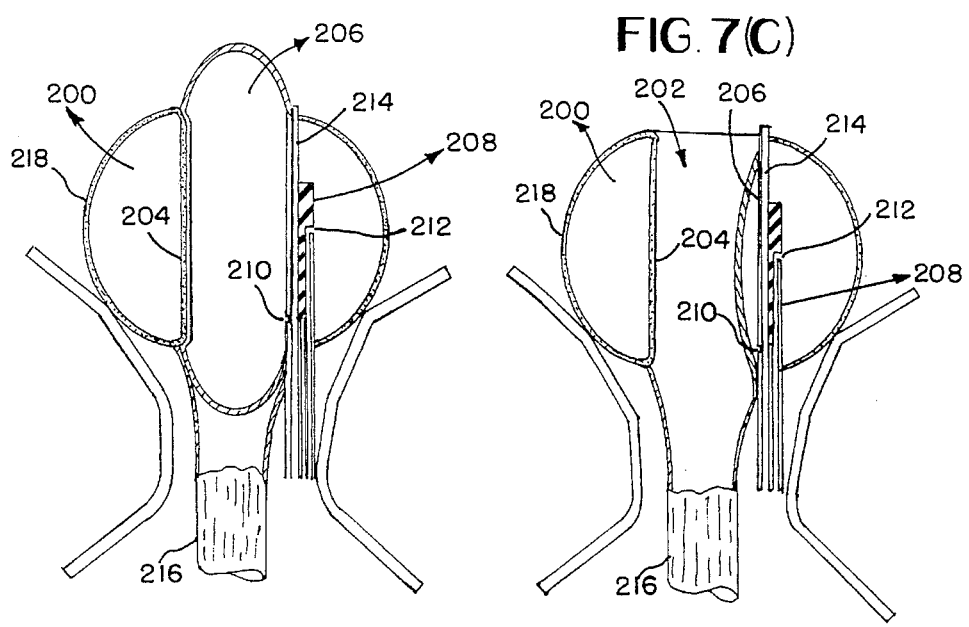
FIG.7(B)
FIG.7(C)

MULTIPURPOSE COLOSTOMY DEVICE HAVING BALLOONS ON AN END THEREOF

BACKGROUND OF THE INVENTION

1. Field of the Invention

The present invention relates to a multipurpose colostomy device for fixing in the stoma or rectum and more particularly, to a colostomy device having balloons on an end thereof for preventing leakage particularly of liquids and gases, irrigating a stool through a drainage tube thereof, and assembling an enema device and a fluid container therewith.

2. Description of Related Art

Various types of colostomy bags are well known in the art. Such colostomy bags can be securely coupled to an adhesive dressing that fits around the stoma as a kind of collector from the anal canal. Such colostomy bags are shown in British Patent No. 1,099,455, British Patent 1,212,904, and U.S. Pat. No. 4,460,363. However, since such conventional colostomy bags are only a collecting container of waste materials from the stoma, they do not have a drainage hose and an enema device for patients who cannot control the bowel movement and who should not move for emptying the bowel. Furthermore, such conventional colostomy bags suffer from a number of problems. For example, it is difficult to attach the colostomy bag on the outside of the abdomen and to carry the colostomy bag having the stool, and it is complicated to apply the enema device or replace the same on the colostomy bag.

SUMMARY OF THE INVENTION

Accordingly, it is an object of the present invention to provide a multipurpose colostomy device for fixing in the stoma of patients with colostomy or ileostomy, which eliminates the above problems for controlling stool passage encountered with conventional colostomy devices, and the rectum of the patient who cannot control his bowel movement such as hepatic coma, CVA in ICU, pelvic bone, spine, and other long bone fractures.

Another object of the present invention is to provide an improved colostomy device including external and internal balloons, a drainage, and a triple lumened catheter for preventing leaking particularly of liquids and gases, irrigating stools through the drainage hose and assembling with an enema device and a fluid container through the triple lumened catheter thereof.

A further object of the present invention is to provide a multipurpose colostomy device which is simple in structure, inexpensive to manufacture, easy to use, and durable in construction.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention is merely directed to a multipurpose colostomy device for fixing in the stoma, which includes an internal balloon for control of a stool passage and infusing enema irrigation fluid, an external balloon fitted around the stoma for preventing liquid from leaking through the anal canal, a drainage tube operatively assembled with a joint tube for draining irrigated stool, and a triple lumened catheter for assembling an air pumping device with an enema device.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 5 is a sectional view of the multipurpose colostomy device so as to illustrate the cross-sectional view thereof according to the present invention;

FIG. 6(A) is a cross-sectional view of FIG. 5, taken along line A—A;

FIG. 6(B) is a cross-sectional view of FIG. 5, taken along line B—B;

FIG. 6(C) is a cross-sectional view of FIG. 5, taken along line C—C;

FIG. 6(D) is a cross-sectional view of FIG. 5, taken along line D—D;

FIG. 6(E) is a cross-sectional view of FIG. 5, taken along line E—E;

FIG. 7(A) is a somewhat diagrammatic sectional view of a second embodiment of the multipurpose colostomy device according to the present invention before inserting the multiple purpose colostomy device into the rectum;

FIG. 7(B) is a somewhat diagrammatic sectional view of the second embodiment of the multipurpose colostomy device according to the present invention showing, after the multipurpose colostomy device inserts into the rectum, the inflated internal and external balloons; and FIG. 7(C) is a somewhat diagrammatic sectional view of the second embodiment of the multipurpose colostomy device according to the present invention showing, after the multipurpose colostomy device inserts into the rectum, the deflated internal balloon for passage of the irrigated stool.

DETAILED DESCRIPTION OF THE PREFERRED EMBODIMENTS

Figure 1A:
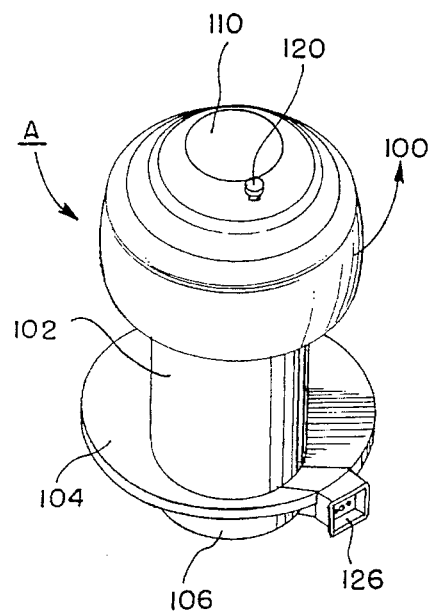
FIG. 1(A) is a perspective view of a multipurpose colostomy device showing inflated internal and external balloons according to the present invention.
Figure 1B:
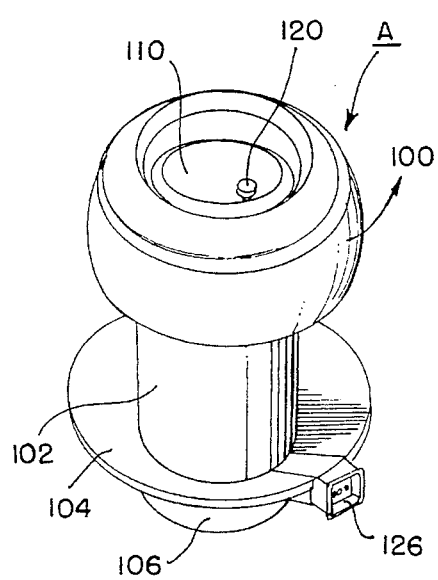
FIG. 1(B) is a perspective view of the multipurpose colostomy device showing a deflated internal balloon and an inflated external balloon according to the present invention.

Referring now in detail to the drawings for the purpose of illustrating preferred embodiments of the present invention, the multipurpose colostomy device A as shown in FIGS. 1(A), 1(B), 2, and 3 includes an external balloon 100 having a ring configuration, an internal balloon 110 disposed within the ring configured external balloon 100, a connecting tube 102 disposed under the external and internal balloons 100 and 110, and a supporting plate 104 and a joint tube 106 disposed under the connecting tube 102.

The external and internal balloons 100 and 110 are each formed of a thin membrane, and are made of elastic material. The connecting tube 102 is made of elastic material so that it is expanded when the user produces a stool and it is contracted when the user does not produce a stool. The supporting plate 104 and a joint tube 106 are made of resilient material.

As shown in FIGS. 5, 6(B), and 6(C), a supply tube 108 is made of a resilient material, and is disposed at an inside wall of the external balloon 100. The supply tube 108 is passed through the internal balloon 110. Also, the supply tube 108 is provided with a first air opening 112 communicating with the internal balloon 110 and a second air opening 114 communicating with the external balloon 100.

As shown in FIGS. 5 and 6(A), an enema fluid infusion tube 118 having an enema fluid one-way valve 120 disposed on the top thereof, is disposed in parallel with the supply tube 108. Also, the first enema fluid infusion tube 118 is higher than the internal balloon 110.

Figure 3:
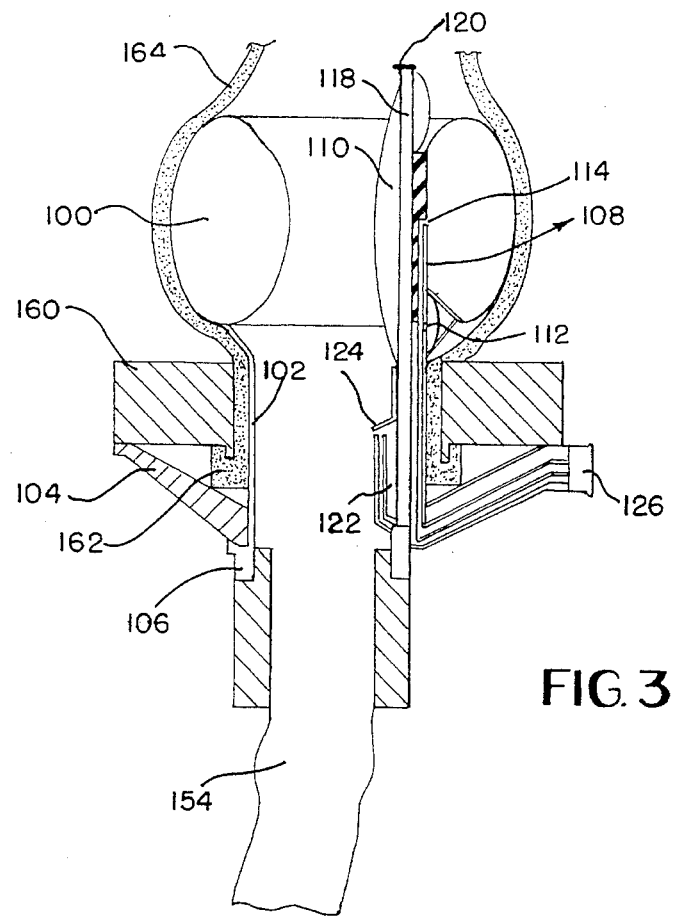
FIG. 3 is a sectional view of the multipurpose colostomy device according to the present invention showing the deflated internal balloon from FIG. 2.

As shown in FIGS. 3, 5 and 6(E), a washing fluid infusion tube 122 is located in parallel with the enema fluid infusion tube 118 at the lower portion of the enema fluid infusion tube 118. The washing fluid infusion tube 122 has a washing fluid one-way valve 124 disposed on the top thereof and disposed within the connecting tube 102.

As shown in FIGS. 5 and 6(E), a holder 126 is disposed at ends of the supply tube 108, the enema fluid infusion tube 118, and the washing fluid infusion tube 122. At this point, the supply tube 108, the enema fluid infusion tube 118, and the washing fluid infusion tube 122 have a C-shaped configuration at the lower portion thereof, respectively, so as to match with the holder 126 located at one side of the supporting plate 104.

Figure 4:
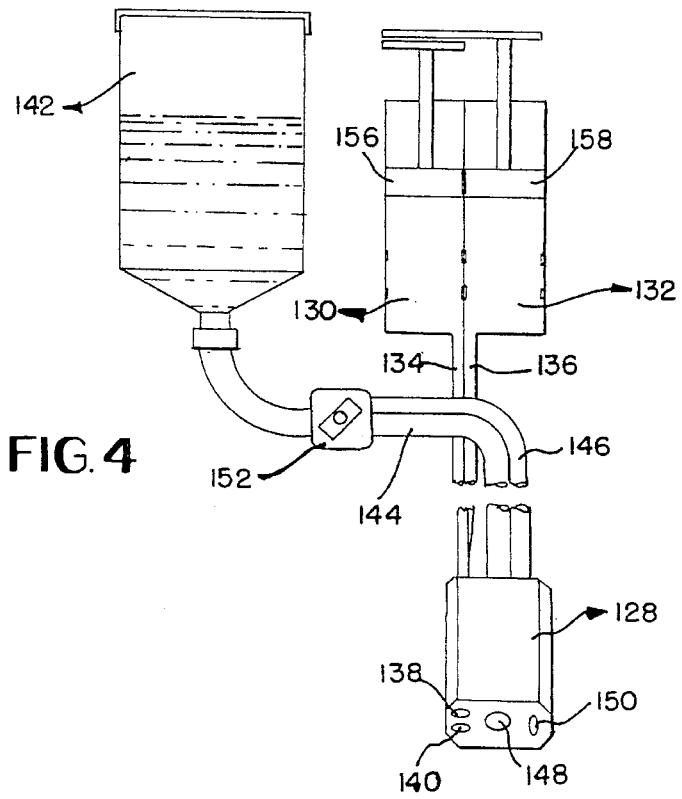
FIG. 4 is a somewhat diagrammatic side view of an air pumping device and an enema device for assembling with a holder of the colostomy body according to the present invention.

As shown in FIG. 4, if necessary, the multipurpose colostomy device A is provided with a socket 128 engaged with the holder 126 thereof. The socket 128 is provided with a first air cylinder 130 having a first piston 156, and a second air cylinder 132 having a second piston 158, which is connected to a first air opening 138 through a first air tube 134, and a second air opening 140 through a second air tube 136, respectively.

The socket 128 is further provided with a fluid container 142 connected to a first fluid opening 148 through a first fluid tube 144 and a second fluid opening 150 through a second fluid tube 146. The first fluid tube 144 and the first fluid opening 148 have a larger size than the second fluid tube 146 and the second fluid opening 150 (FIG. 4). A changeover switch 152 can optionally open and close the first and second fluid tubes 144 and 146, respectively for passing the fluid in a fluid container 142.

Figure 2:
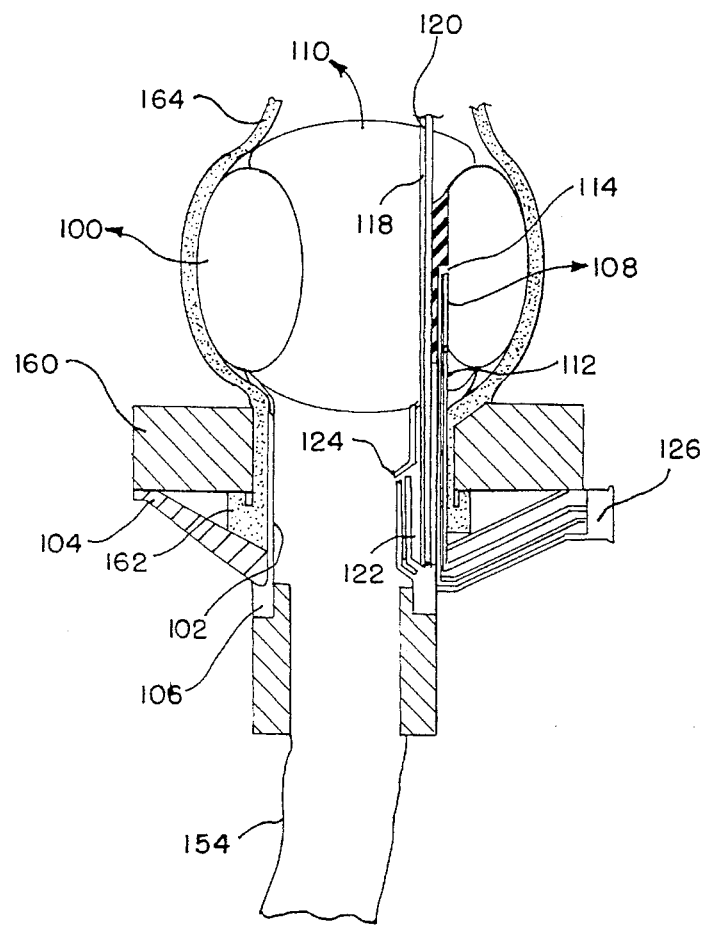
FIG. 2 is a sectional view of the multipurpose colostomy device according to the present invention, which is applied to the stoma such as the colostomy or ileostomy.

As shown in FIG. 2, if necessary, the joint tube 106 can tightly receive a drainage hose 154 or a collecting container (not shown). If the joint tube 106 does not connect to the drainage hose 154, a closing cap (not shown) can be tightly closed around the end of the joint tube 106. The drainage hose 154 is made of a foldable, thin material such as vinyl, rubber or silicon material.

As shown in FIG. 1, the multipurpose colostomy device A according to the present invention operates as follows: the multipurpose colostomy device A of the present invention, mainly applies to patients who have the stoma 162 disposed on an abdominal wall 160 which is connected to the colon 164, or ileum who are enema patients and cannot control their bowel movement, CVA or ICU and pelvic bone, spine, and other long bone fractures.

After the multipurpose device A inserts into the stoma 162, if the user pushes the first and second pistons 156 and 158, repeatedly, the air is infused into the external and internal balloons 100 and 110 through the first and second air tubes 134 and 136, the first and second air openings 138 and 140 of the socket 128, and the second and first air openings 114 and 112 of the supply tube 108. At this time, when the external and internal balloons 100 and 110 inflate, the inflated external balloon 100 adheres closely to the colon 164 for closing a space disposed between the external balloon 100 and the colon 164, and the inflated internal balloon 110 adheres closely to the inflated external balloon 100 for closing a space disposed between the external and internal balloons 100 and 110. Finally, the multipurpose colostomy device A fixes in the opening of the stoma.

When the stool is to discharge from the stoma 162, after the drainage hose 154 having the collecting container (not shown) is connected to the joint tube 106, by pulling the second piston 158, the air of the internal balloon 110 discharges for making the deflated internal balloon 110 as shown in FIG. 3. At this time, the colostomy device A opens and the stool collects in the collecting container through the connecting tube 102 and the drainage hose 154.

When the discharging of the stool finishes, the changeover switch 152 adjusts to supply the washing fluid in the fluid container 142 to the connecting tube 102 which is contaminated by the discharging of the stool through the second fluid tube 146, the second fluid opening 150 of the socket 128, the washing fluid infusion tube 122 and the washing fluid infusion valve 124.

After the connecting tube 102, by pushing the second piston 158, the internal balloon 110 is inflated to close the stoma opening. Thereafter, the drainage hose 154 having the collecting container is separated from the colostomy device A and the opening of the stoma 162 is closed by a cap (not shown). At this time, if desired, the air pressure of the external balloon 100 can be controlled by discharging of air thereof by using the first piston 156 so as not to press to the colon 164 or the rectum.

In order to infuse the enema fluid into the colon 164, the changeover switch 152 adjusts to supply the enema fluid in the fluid container 142 to the colon 164 (FIG. 4). At this point, similar to the above mentioned washing fluid, the enema fluid in the fluid container 142 is supplied to the colon 164 through the first fluid tube 144, the first fluid opening 148 of the socket 128, the enema fluid infusion tube 118, and an enema fluid valve 120 (FIG. 2).

In the multipurpose colostomy device according to the present invention, since the enema fluid and washing fluid one-way valves 120 and 124 enable a forward flow, the valves 120 and 124 prevent the fluid from flowing backward. Also, the holder 126 has a one-way valve (not shown) so that even though the socket 128 separates from the holder 126, the air in the external and internal balloons 100 and 110 do not leak through the socket 128.

Accordingly, if the drainage hose 154 and the socket 128 having the fluid container 142 and air infusion device separate from the multipurpose colostomy device A, the connecting tube 106, the supporting plate 104, and the holder 126 of supply tube 108 appear at the stoma 162. Therefore, if the cap closes the connecting tube 106, there is no problem for patients who have the stoma 162 and others, to have an active life.

During activity, anytime, when the stool discharges, after taking out the cap from the connecting tube 106, putting the drainage hose 154 is placed into the connecting tube 106 and the socket 12 engages with the holder 126. Thereafter, the internal balloon 110 is deflated by expelling air from the internal balloon 110. It is easy to operate the colostomy device A of the present invention.

Referring now to FIGS. 7(A), 7(B), and 7(C), there is another embodiment of the multipurpose colostomy device A without the supporting plate 104 of FIG. 2 according to the present invention. The external balloon 200 has an outside wall 218 having a thin wall and an inside wall 204 having a thick wall. The inside wall 204 is made of resilient material. By deflating the external and internal balloons 200 and 206, only the outside wall 218 expands and the inside wall 204 maintains an original position so that the inside wall 204 of the external balloon 200 and internal balloon 206 are tightly fixed in the rectum as shown in FIG. 7(B).

When the stool is to discharge from the rectum 7(B), the internal balloon 206 is deflated by discharging air in the internal balloon 206 through the first air opening 112 of the supply tube 208. Therefore, the connecting tube 202 opens and the stool can be collected in the collecting container (not shown) through the drainage hose 216 as shown in FIG. 7(C).

After discharging of the stool finishes, the contaminated connecting tube 202 can be washed by washing fluid through the washing fluid infusion tube and the washing fluid infusion on/off valve (not shown). Also, the enema fluid can be infused into the colon through the enema fluid infusion tube 214 and the enema fluid infusion on/off valve (not shown).

Accordingly, the multipurpose colostomy device of the present invention is very useful for patients who have the stoma 162, who cannot control their bowel movements, and who should not move for emptying, such as hepatic coma, CVA in ICU, pelvic bone, spine, and other long bone fractures.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A multipurpose colostomy device for fixing in the stoma or the rectum of a human body, said colostomy device comprising:

an internal balloon;

an external balloon surrounding said internal balloon;

a connecting tube disposed under said internal and external balloons;

a joint tube disposed under said connecting tube;

an annular supporting plate upwardly disposed between said connecting tube and said joint tube, for fixing the multipurpose colostomy device to the abdominal wall of the stoma;

a supply tube vertically disposed in said connecting tube and between said internal and said external balloons for communicating with the connecting tube and the internal and external balloons, said supply tube having a holder disposed at an end of a bending portion thereof, for assembling with a socket connected to a fluid tank and an air pump wherein said supply tube includes a pair of air passages communicating with said internal and external balloons through a first air opening and a second air opening, respectively, said supply tube further including an enema fluid passage passed through said internal balloon for communicating with the colon through an enema one-way valve, and wherein said enema fluid passage includes an enema fluid one-way valve located over said internal balloon and in the colon; and means for inflating and deflating the internal and external balloons and supplying enema irrigating fluid, such that the multipurpose colostomy device can effectively close the stoma, prevent leakage, particularly liquids and gases, discharge the stool, wash the contaminated connecting tube after discharging of stool, and irrigate the colon with enema fluid.

2. The multipurpose colostomy device of claim 1, further comprising a washing fluid passage disposed in parallel with said enema passage for communicating with the connecting tube, and said means for inflating and deflating additionally supplying washing fluid, wherein said washing fluid passage includes a washing fluid one-way valve disposed on an upper end thereof and in said connecting tube.

3. The multipurpose colostomy device of claim 1, wherein said socket engaged with said holder, includes first and second air cylinders for infusing air to discharging air from the internal and external balloons, and a fluid tank for infusing enema fluids to the connecting tube and the colon, respectively.

4. The multipurpose colostomy device of claim 3, wherein said first cylinder includes a first piston and connects to a first air opening through a first air tube, and said second cylinder includes a second piston and connects to a second air opening through a second air tube.

5. The multipurpose colostomy device of claim 3, wherein said fluid tank is provided with a changeover switch and connects a first opening through a first fluid tube and a second fluid opening through a second fluid tube.

6. The multipurpose colostomy device of claim 1, wherein said external balloon has an inside wall and an outside wall, said inside wall having a thick wall and said outside wall having a thin wall, so that by inflating the external balloon, the outside wall expands very well and the inside wall maintains an original figure so as to tightly fix in the rectum.

7. A multipurpose colostomy device for fixing in the rectum of a human body, said colostomy device comprising:

an internal balloon;

an external balloon surrounding said internal balloon;

a connecting tube disposed under said internal and external balloons;

a joint tube disposed under said connecting tube;

a supply tube vertically disposed in said connecting tube and between said internal and said external balloons for communicating with the connecting tube and the internal and external balloons, said supply tube having a holder disposed at an end of a bending portion thereof, for assembling with a socket connected to a fluid tank and an air pump, wherein said supply tube includes a pair of air passages communicating with said internal and external balloons through a first air opening and a second air opening, respectively, said supply tube further including an enema fluid passage passed through said internal balloon for communicating with the colon through an enema one-way valve, wherein said enema fluid passage includes an enema fluid one-way valve located over said internal balloon and in the colon; and means for inflating and deflating the internal and external balloons and supplying enema irrigating fluid, such that the multipurpose colostomy device can effectively close the stoma, prevent leakage, particularly liquids and gases, discharge the stool, wash the contaminated connecting tube after discharging of stool, and irrigate the colon with enema fluid.

8. The multipurpose colostomy device of claim 7, further comprising a washing fluid passage disposed in parallel with said enema passage for communicating with the connecting tube, and said means for inflating and deflating additionally supplying washing fluid, wherein said washing fluid passage includes a washing fluid one-way valve disposed on an upper end thereof and in said connecting tube.

9. The multipurpose colostomy device of claim 7, wherein said socket engaged with said holder, includes first and second air cylinders for infusing air to discharging air from the internal and external balloons, and a fluid tank for infusing washing and enema fluids to the connecting tube and the colon, respectively.

10. The multipurpose colostomy device of claim 9, wherein said first cylinder includes a first piston and connects to a first air opening through a first air tube, and said second cylinder includes a second piston and connects to a second air opening through a second air tube.

11. The multipurpose colostomy device of claim 9, wherein said fluid tank is provided with a changeover switch and connects a first opening through a first fluid tube and a second fluid opening through a second fluid tube.

12. The multipurpose colostomy device of claim 7, wherein said external balloon has an inside wall and an outside wall, said inside wall having a thick wall and said outside wall having a thin wall, so that by inflating the external balloon, the outside wall expands very well and the inside wall maintains an original figure so as to tightly fix in the rectum.

* * * * *